(12) United States Patent
Morioka

(10) Patent No.: US 11,638,682 B2
(45) Date of Patent: May 2, 2023

(54) HAIR COSMETIC

(71) Applicant: KAO CORPORATION, Tokyo (JP)

(72) Inventor: Tomoki Morioka, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/743,528

(22) PCT Filed: Jul. 7, 2016

(86) PCT No.: PCT/JP2016/070191
§ 371 (c)(1),
(2) Date: Jan. 10, 2018

(87) PCT Pub. No.: WO2017/010409
PCT Pub. Date: Jan. 19, 2017

(65) Prior Publication Data
US 2018/0200169 A1 Jul. 19, 2018

(30) Foreign Application Priority Data
Jul. 10, 2015 (JP) .............................. JP2015-138223

(51) Int. Cl.
| | | |
|---|---|---|
| *A61Q 5/12* | (2006.01) | |
| *A61K 8/41* | (2006.01) | |
| *A61K 8/31* | (2006.01) | |
| *A61K 8/37* | (2006.01) | |
| *A61K 8/36* | (2006.01) | |
| *A61K 8/89* | (2006.01) | |
| *A61K 8/42* | (2006.01) | |
| *A61K 8/896* | (2006.01) | |
| *A61K 8/9789* | (2017.01) | |
| *A61K 8/9794* | (2017.01) | |
| *A61K 8/34* | (2006.01) | |
| *A61K 8/365* | (2006.01) | |
| *A61K 8/58* | (2006.01) | |
| *A61K 8/92* | (2006.01) | |

(52) U.S. Cl.
CPC ................ *A61K 8/416* (2013.01); *A61K 8/31* (2013.01); *A61K 8/342* (2013.01); *A61K 8/345* (2013.01); *A61K 8/36* (2013.01); *A61K 8/365* (2013.01); *A61K 8/37* (2013.01); *A61K 8/42* (2013.01); *A61K 8/585* (2013.01); *A61K 8/89* (2013.01); *A61K 8/896* (2013.01); *A61K 8/922* (2013.01); *A61K 8/9789* (2017.08); *A61K 8/9794* (2017.08); *A61Q 5/12* (2013.01)

(58) Field of Classification Search
None
See application file for complete search history.

(56) References Cited

U.S. PATENT DOCUMENTS

| | | | |
|---|---|---|---|
| 5,002,761 A * | 3/1991 | Mueller | A61K 8/365 424/70.1 |
| 2001/0053374 A1 | 12/2001 | Dalrymple et al. | |
| 2002/0064510 A1 | 5/2002 | Dalrymple et al. | |
| 2002/0159966 A1* | 10/2002 | Doi | A61K 8/416 424/70.28 |
| 2004/0116311 A1 | 6/2004 | Luo et al. | |
| 2011/0070175 A1 | 3/2011 | Herrwerth et al. | |
| 2012/0095115 A1 | 4/2012 | Kawa et al. | |
| 2012/0276035 A1 | 11/2012 | Lehman, Jr. | |
| 2013/0059929 A1 | 3/2013 | Koehler et al. | |
| 2013/0259821 A1 | 10/2013 | Henning et al. | |
| 2013/0276810 A1* | 10/2013 | Hoffmann | A61K 8/44 132/208 |
| 2014/0137884 A1 | 5/2014 | Lehman | |
| 2015/0044158 A1 | 2/2015 | Farwick et al. | |
| 2015/0315123 A1 | 11/2015 | Schuch et al. | |

FOREIGN PATENT DOCUMENTS

| | | |
|---|---|---|
| CN | 101612102 B | 11/2013 |
| DE | 10 2006 030 135 A1 | 12/2009 |

(Continued)

OTHER PUBLICATIONS

International Search Report dated Aug. 23, 2016, in PCT/JP2016/070191 filed Jul. 7, 2016.
Extended European Search Report dated Jan. 2, 2019 in European Patent Application No. 16824389.7, 8 pages.

(Continued)

*Primary Examiner* — Jyothsna A Venkat
(74) *Attorney, Agent, or Firm* — Oblon, McClelland, Maier & Neustadt, L.L.P.

(57) ABSTRACT

Provided is a rinse-off-type hair cosmetic composition used by being applied to hair and then washed away, the hair cosmetic composition comprising: the ingredients (A) to (C) below, and water, wherein a molar ratio of the ingredient (B) to the ingredient (A), (B)/(A), is less than 3, and a mass ratio of the ingredient (C) to the ingredient (A), (C)/(A), is less than 1:

(A) an amido-cationic surfactant represented by formula (1)

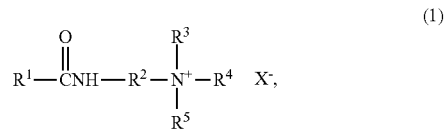

(1)

wherein $R^1$ represents a $C_{11-17}$-alkyl group or alkenyl group, $R^2$ represents a $C_{2-4}$-alkylene group, $R^3$, $R^4$, and $R^5$ independently represent a $C_{1-3}$-alkyl group, an alkenyl group, or hydroxyalkyl group, and $X^-$ represents an anion;
(B) a fatty alcohol having 14 to 18 carbon atoms; and
(C) a silicone.

21 Claims, 1 Drawing Sheet

(56) References Cited

FOREIGN PATENT DOCUMENTS

| | | | |
|---|---|---|---|
| DE | 10 2008 030 136 A1 | 12/2009 | |
| EP | 2 138 156 A1 | 12/2009 | |
| EP | 2138156 A1 * | 12/2009 | ............... A61Q 5/12 |
| EP | 2 881 381 A1 | 6/2015 | |
| EP | 2 883 533 A1 | 6/2015 | |
| JP | 11-286415 A | 10/1999 | |
| JP | 2000-143459 A | 5/2000 | |
| JP | 2006-265205 A | 10/2006 | |
| JP | 2013-6803 A | 1/2013 | |
| WO | WO 00/45787 A1 | 8/2000 | |
| WO | WO 2004/061061 A1 | 7/2004 | |
| WO | WO 2014/071141 A | 5/2014 | |

OTHER PUBLICATIONS

Water-resistant cosmetic formulations comprising a hydrophobically modified vinylpyrrolidone copolymer, IP. com Journal, IP.com Inc., West Henrietta, NY, US, XP013146751, Aug. 2, 2011, pp. 1-251 and cover page.

Technical data sheet of the commercial product "Varlsoft PATC" (Evonik Industries), published in Apr. 2008, 5 pages.

* cited by examiner

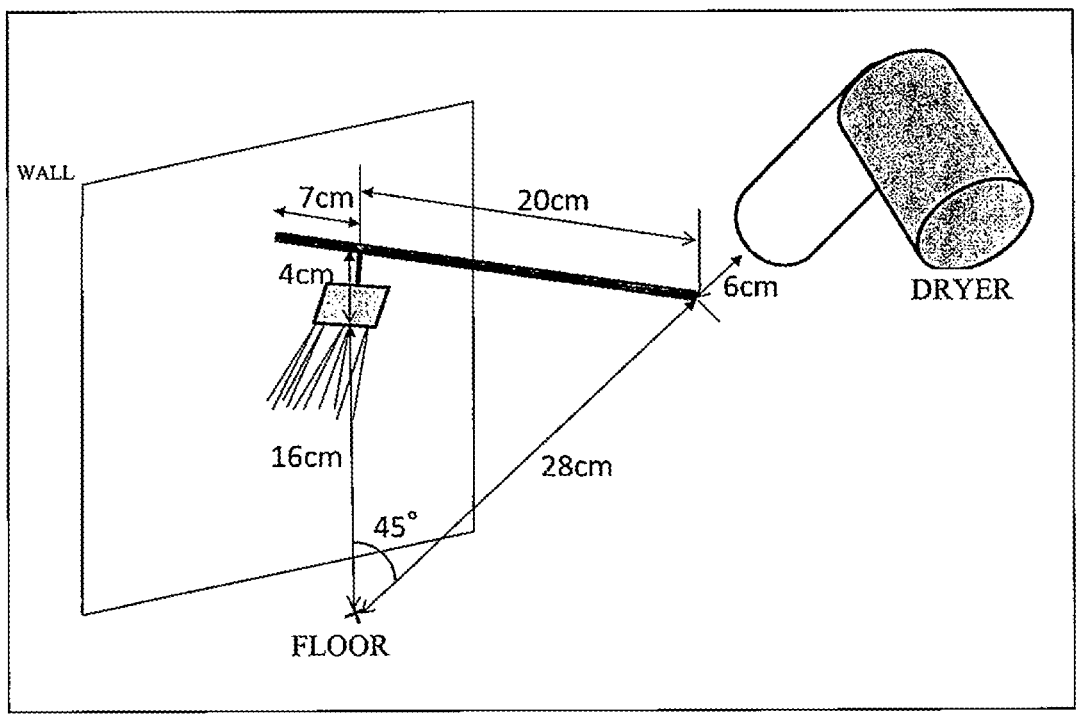

HAIR COSMETIC

FIELD OF THE INVENTION

The present invention relates to a rinse-off-type hair cosmetic composition which is applied to hair and washed away.

BACKGROUND OF THE INVENTION

A rinse-off-type hair cosmetic composition which is used after shampooing and is washed away such as hair rinses and hair conditioners, contain a cationic surfactant and a fatty alcohol as major components and are intended to condition the surface of the hair by giving smoothness or moist feeling to the hair. For example, Patent Documents 1 to 4 disclose hair conditioners or the like containing a cationic surfactant, a fatty alcohol, a silicone, or the like.
(Patent Document 1) JP-A-2000-143459
(Patent Document 2) JP-A-11-286415
(Patent Document 3) JP-A-2002-536314
(Patent Document 4) JP-A-2006-265205

SUMMARY OF THE INVENTION

The present invention provides a rinse-off-type hair cosmetic composition used by being applied to hair and then washed away, the rinse-off-type hair cosmetic composition comprising: the ingredients (A) to (C) below, and water, wherein a molar ratio of the ingredient (B) to the ingredient (A), (B)/(A), is less than 3, and a mass ratio of the ingredient (C) to the ingredient (A), (C)/(A), is less than 1:
(A) amido-cationic surfactant represented by formula (1):

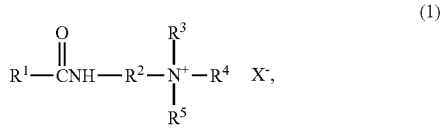

wherein $R^1$ represents a linear or branched alkyl group or alkenyl group having 11 to 17 carbon atoms, $R^2$ represents a linear or branched alkylene group having 2 to 4 carbon atoms, $R^3$, $R^4$, and $R^5$ independently represent a linear or branched alkyl group, alkenyl group, or hydroxyalkyl group having 1 to 3 carbon atoms, and $X^-$ represents an anion;
(B) a fatty alcohol having 14 to 18 carbon atoms; and
(C) a silicone.

BRIEF DESCRIPTION OF DRAWING

FIG. 1 is a view illustrating an apparatus used for evaluating the ease of hair's separating each other in Examples.

DETAILED DESCRIPTION OF THE INVENTION

In recent years, hair damage is getting serious which is caused by hair setting or the like using heat such as a hair iron and a dryer, which is habitualized mainly in young women, in addition to chemical treatment such as a hair color and a perm. The hair damage is known to involve the loss of 18-MEA (18-methyl eicosanoic acid), which is a fatty acid covering the hair surface, to thereby cause hydrophilization of the hair surface and an increase in surface friction. The damaged and thus hydrophilized hair not only lose smoothness but also become difficult to get dry after shampooing, so that blow-drying or the like requires a long time, which causes a physical burden. Further, wet and damaged hair is easily entangled, and hooking which occurs during the blow-drying causes further accumulation of damage and a psychological burden of the consumer.

However, the hair conditioners disclosed in Patent Documents 1 to 3 do not have any effects of improving the drying speed of the hair after shampooing, and there is neither description nor suggestion on the drying speed in these Documents.

Further, Patent Document 4 discloses that the hair conditioning composition disclosed therein provides excellent drying speed after application to dry hair and can give a smooth feeling and softness to the hair. However, the hair conditioning composition specifically disclosed therein is only the leave-on-type which is not washed away, and the effect of "rapid drying after application" in the disclosure means rapid drying of the hair conditioning composition itself. Accordingly, this Document includes no suggestion on the drying speed of hair after using a rinse-off-type hair cosmetic composition which itself is washed away after application to the hair.

Therefore, the present invention relates to a rinse-off-type hair cosmetic composition which is applied to the hair after shampooing and then washed away and enables the wet hair to dry within a short time.

As a factor to increase the drying speed of the hair after shampooing, "ease of separating hair" is important. Specifically, when the hair are dried with a towel, separating the hair allows the contact area of hair with the towel to increases, so that the moisture of the hair is rapidly absorbed in the towel, and also during blow-drying (also in air drying), separating the hair allows the contact area of hair with air to increases, so that the moisture of the hair rapidly evaporates.

In a common rinse-off-type hair cosmetic composition which is used after shampooing and washed away, such as hair rinses and hair conditioners, a cationic surfactant and a fatty alcohol form a stable α-gel, and therefore a silicone contained together with these ingredients remain unevenly on the surface of the hair after being washed with water and exhibit adherence to cause inhibition of the separating.

The inventor has found that the ease of separating hair can be improved by employing an amide cationic surfactant having high hydrophilicity as the cationic surfactant in the rinse-off-type of hair cosmetic composition which is used after shampooing and is washed away, and adjusting a compounding ratio between it and a fatty alcohol to fall within a certain range. Further, the inventor has found that, when the compounding ratio between the amido-cationic surfactant and a silicone is adjusted to fall within a certain range, the silicone remaining on the hair surface after washing with water forms a uniform adsorption membrane with no stickiness and high water repellency to thereby promote the separating of hair, so that the drying speed of the hair is dramatically improved.

In the amido-cationic surfactant which serves as the ingredient (A), $R^1$ in formula (1) is preferably a linear or branched alkyl group or alkenyl group having 13 to 17 carbon atoms, further preferably having 15 to 17 carbon atoms. $R^2$ is preferably an ethylene group or a trimethylene group. $R^3$, $R^4$, and $R^5$ are preferably independently a methyl group, an ethyl group, a hydroxyethyl group, or a hydroxypropyl group, more preferably a methyl group or an ethyl group, further preferably a methyl group. Examples of the anion represented by $X^-$ include halide ions such as $Cl^-$ and Br⁻, alkyl sulfate ions having 1 to 5 carbon atoms (such as $CH_3SO_4^-$, $C_2H_5SO_4^-$, and $C_3H_7SO_4^-$), and alkyl carbonate ions ($CH_3CO_3^-$). Among them, Cl⁻, Br⁻, $CH_3SO_4^-$, $C_2H_5SO_4^-$, and $CH_3CO_3^-$ are preferable, and Cl⁻ and Br⁻ are further preferable.

Specific preferable examples of the amido-cationic surfactant which serves as the ingredient (A) include the compound below:

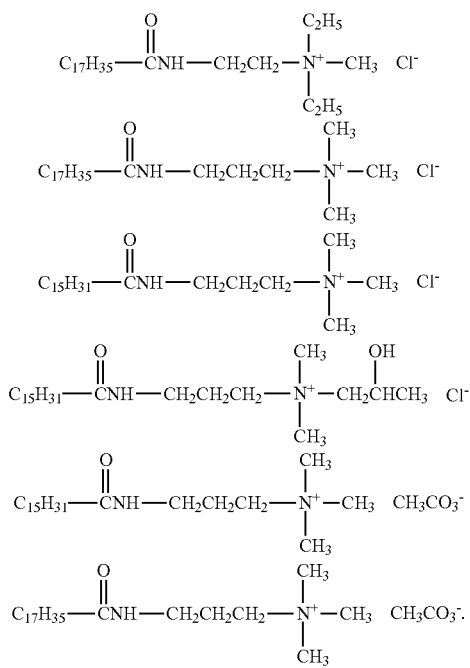

The amido-cationic surfactant which serves as the ingredient (A) is obtained by obtaining alkyl amidoamine through a reaction of a fatty acid, a fatty acid lower alkyl ester, or a fatty acid derivative such as oils and fats with N,N-dialkylamine, and quaternizing the alkyl amidoamine with a quaternizing agent such as an alkyl halide. The reaction molar ratio of the fatty acid or the derivative thereof with N,N-dialkylamine is preferably N,N-dialkylamine/the fatty acid or the derivative thereof=1.0 to 3.0, further preferably 1.0 to 2.0. The reaction temperature is preferably 40 to 200° C., further preferably 50 to 180° C. It is possible to blend the fatty acid or the derivative thereof and N,N-dialkylamine in the same reactor at a time and react them after the temperature is raised. However, when the reaction is performed while adding N,N-dialkylamine to the fatty acid or the derivative thereof whose temperature has been raised, the reactivity can be further enhanced and high purity alkyl amidoamine can be obtained. Further, the reaction can be performed more efficiently within a short time by use of an acid catalyst such as sulfuric acid and p-toluenesulfonic acid in the case of the fatty acid or use of an alkali catalyst such as sodium methylate in the case of the fatty acid derivative. The amido-cationic surfactant which serves as the ingredient (A) can be used alone, or two or more thereof may be used in combination.

In view of the stability of the system, the content of the ingredient (A) in the hair cosmetic composition of the present invention is preferably 0.1 mass % or more, more preferably 1 mass % or more, further preferably 2 mass % or more, and in view of the spreadability in application, it is preferably 10 mass % or less, more preferably 7 mass % or less, further preferably 6 mass % or less, further preferably 5 mass % or less.

As the fatty alcohol having 14 to 18 carbon atoms which serves as the ingredient (B), either a saturated fatty alcohol or an unsaturated fatty alcohol can be used. Specific examples thereof include myristyl alcohol, cetyl alcohol, stearyl alcohol, and oleyl alcohol, and cetyl alcohol and stearyl alcohol are particularly preferable. These can be used alone, or two or more of them can be used in combination.

In view of the ease of separating hair and the rapid drying of wet hair, the molar ratio of the ingredient (B) to the ingredient (A), (B)/(A), in the hair cosmetic composition of the present invention is less than 3, preferably 2.9 or less, more preferably 2.8 or less, further preferably 2.7 or less, and in view of the stability of the system and the smoothness in application, it is preferably 2 or more, more preferably 2.2 or more, further preferably 2.4 or more.

Further, in view of the stability of the hair cosmetic composition, a specific content of the ingredient (B) in the hair cosmetic composition of the present invention is preferably 0.5 mass % or more, more preferably 1 mass % or more, further preferably 3 mass % or more, further preferably 4 mass % or more, further preferably 5 mass % or more, and in view of the spreadability in application, it is preferably 15 mass % or less, more preferably 10 mass % or less, further preferably 8 mass % or less.

Examples of the silicone which serves as the ingredient (C) include dimethyl polysiloxane, cyclic silicone, amino-modified silicone, dimethiconol, polyether-modified silicone, polyglycidol-modified silicone, methylphenyl polysiloxane, fatty acid-modified silicone, alcohol-modified silicone, alkoxy-modified silicone, epoxy-modified silicone, fluorine-modified silicone, and alkyl-modified silicone, and in view of the ease of separating hair and the rapid drying of wet hair, dimethyl polysiloxane and amino-modified silicone are preferable. Further, in view of the dispersibility in the hair cosmetic composition, the weight-average molecular weight of the silicone which serves as the ingredient (C) is preferably 200,000 or less, more preferably 180,000 or less, further preferably 100,000 or less, further preferably 70,000 or less. Further, in view of the smooth hair, the molecular weight of the silicone which serves as the ingredient (C) is preferably 236 or more, more preferably 450 or more.

For separating hair, achieving smoothness in application, and eliminating stickiness, the mass ratio of the ingredient (C) to the ingredient (A), (C)/(A), in the hair cosmetic composition of the present invention is less than 1, preferably 0.8 or less, more preferably 0.5 or less, and for separating hair, enhancing the water-repellent effect on the hair surface, rapidly drying wet hair, and achieving smoothness in application, it is preferably 0.01 or more, more preferably 0.1 or more, further preferably 0.2 or more.

Further, in view of the water-repellent effect on the hair surface, a specific content of the ingredient (C) in the hair cosmetic composition of the present invention is preferably 0.1 mass % or more, more preferably 0.3 mass % or more, further preferably 0.5 mass % or more, and in view of the ease of separating hair, it is preferably 10 mass % or less, more preferably 5 mass % or less, further preferably 3 mass % or less, further preferably 2 mass % or less.

The hair cosmetic composition of the present invention can further contain a monovalent to trivalent fatty alcohol having 1 to 6 carbon atoms or aromatic alcohol having 7 to 10 carbon atoms as the ingredient (D). Examples of such alcohol include isopropyl alcohol, butanediol, propylene glycol, dipropylene glycol, benzyl alcohol, benzyloxyethanol, and phenoxyethanol.

In view of the smoothness in application and the smoothness of hair after drying, the content of the ingredient (D) in the hair cosmetic composition of the present invention is preferably 0.01 mass % or more, more preferably 0.05 mass % or more, further preferably 0.1 mass % or more, further preferably 0.5 mass % or more, and for eliminating stickiness, it is preferably 10 mass % or less, more preferably 5 mass % or less, further preferably 3 mass % or less.

The hair cosmetic composition of the present invention can further contain an organic acid having 8 or less carbon atoms as the ingredient (E). Examples of the organic acid having 8 or less carbon atoms include monocarboxylic acid, dicarboxylic acid, and tricarboxylic acid, and may include hydroxycarboxylic acid. Examples of the monocarboxylic acid include acetic acid, lactic acid, and glycolic acid, examples of the dicarboxylic acid include malonic acid, succinic acid, glutaric acid, adipic acid, maleic acid, fumaric acid, phthalic acid, oxalic acid, malic acid, and tartaric acid, and examples of the tricarboxylic acid include citric acid. Further, examples of the hydroxycarboxylic acid include glycolic acid, lactic acid, malic acid, tartaric acid, and citric acid. Among them, lactic acid, citric acid, malic acid, and glycolic acid are preferable.

In view of the smoothness in application and the effect of promoting the separating hair by combined use with the ingredients (A) to (C), the content of the ingredient (E) in the hair cosmetic composition of the present invention is preferably 0.01 mass % or more, more preferably 0.05 mass % or more, further preferably 0.1 mass % or more, and is preferably 5 mass % or less, more preferably 3 mass % or less, further preferably 1 mass % or less.

In view of the smoothness in application and the smoothness of hair after drying, the hair cosmetic composition of the present invention can further contain a liquid oil agent as the ingredient (F). Examples of the liquid oil agent include hydrocarbons such as liquid paraffin, isoparaffin, and polybutene; ester oils such as isopropyl palmitate; and vegetable oils such as jojoba oil and olive oil. In view of the ease of separating hair, the viscosity (25° C.) of the liquid oil agent is preferably 1 mPa·s or more and it is also preferably 100 mPa·s or less. The viscosity herein is measured at 25° C., using a B-type rotational viscometer (model: digital viscometer TV-10, manufactured by TOKI SANGYO CO., LTD.) and a rotor No. 1, at a rotational speed of 60 rpm.

In view of the smoothness after drying and the effect of enhancing the ease of separating hair by combined use with the ingredients (A) to (C) and further combined use with the ingredients (D) and (E), the content of the ingredient (F) in the hair cosmetic composition of the present invention is preferably 0.01 mass % or more, more preferably 0.05 mass % or more, further preferably 0.1 mass % or more, and for enhancing the ease of separating hair, it is preferably 10 mass % or less, more preferably 5 mass % or less, further preferably 4 mass % or less, further preferably 3 mass % or less, further preferably 2 mass % or less.

[Water]

The hair cosmetic composition of the present invention contains water as a medium. The water accounts for the balance other than the ingredients (A) to (C) and other ingredients.

[Other Optional Ingredients]

The hair cosmetic composition of the present invention can further contain other ingredients which are generally used for hair cosmetic compositions, depending on the purpose. Examples thereof include polymer compounds such as cationized cellulose, hydroxylated cellulose, and highly polymerized polyethylene oxide; non-ionic surfactants such as polyoxyethylene alkyl ether, polyoxyethylene sorbitan fatty acid ester, glycerol mono fatty acid ester, polyglycerin fatty acid ester, polyoxyethylene hardened castor oil, sucrose fatty acid ester, polyglycerin alkyl ether, fatty acid alkanolamide, and alkyl glycoside; waxes such as beeswax, spermaceti, lanolin, and carnaubawax; higher fatty acids such as capric acid, lauric acid, myristic acid, palmitic acid, stearic acid, behenic acid, oleic acid, coconut oil fatty acid, isostearic acid, and isopalmitic acid; oil agents such as isostearyl glyceryl ether and polyoxypropylene butyl ether; anti-dandruff agents such as zinc pyrithione and benzalkonium chloride; pH adjusters; vitamin preparations; disinfectants; anti-inflammatory agents; preservatives; chelating agents; humectants such as panthenol; colorants such as dyes and pigments; extracts such as polar solvent extract of *eucalyptus*, proteins obtained from shells having pearl layers or pearls or hydrolysates thereof, proteins obtained from silk or hydrolysates thereof, protein-containing extract obtained from legume seeds, *Panax ginseng* extract, rice germ extract, Fucus extract, *camellia* extract, aloe extract, *Alpinia zerumbet* leaf extract, and *Chlorella* extract; pearl powder such as titanium mica; refreshing agents such as menthol: perfumes; stainers; ultraviolet absorbers; antioxidants; and other ingredients described in ENCYCLOPEDIA OF SHAMPOO INGREDIENTS (MICELLE PRESS).

[pH]

The pH of the hair cosmetic composition of the present invention is preferably 2.5 or more, further preferably 3.0 or more, and is preferably 6.0 or less, further preferably 5.5 or less, further preferably 5.0 or less. In the present invention, the pH of the hair cosmetic composition is a value at 25° C. when the hair cosmetic composition is diluted with water to 20 fold by mass.

Further, the rinse-off-type hair cosmetic composition of the present invention is used by being applied to hair and then washed away, and examples thereof include hair cosmetic compositions which are used in bathrooms such as hair rinses, hair conditioners, hair treatments, and hair packs.

For conditioning hair using the rinse-off-type hair cosmetic composition of the present invention, the hair cosmetic composition of the present invention may be applied to hair after shampooing and then washed away with water. Thus, the tress is separated easily during drying with towel after rinsing, and wet hair can be dried in a short time.

Preferable aspects of the present invention as to the aforementioned embodiments are further disclosed below.

<1> A rinse-off-type hair cosmetic composition used by being applied to hair and then washed away, the hair cosmetic composition comprising: the ingredients (A) to (C) below, and water, wherein a molar ratio of the ingredient (B) to the ingredient (A), (B)/(A), is less than 3, and a mass ratio of the ingredient (C) to the ingredient (A), (C)/(A), is less than 1:

(A) an amido-cationic surfactant represented by formula (1):

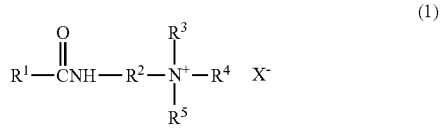

wherein R¹ represents a linear or branched alkyl group or alkenyl group having 11 to 17 carbon atoms, R² represents a linear or branched alkylene group having 2 to 4 carbon atoms, R³, R⁴, and R⁵ independently represent a linear or branched alkyl group, alkenyl group, or hydroxyalkyl group having 1 to 3 carbon atoms, and X-represents an anion;

(B) a fatty alcohol having 14 to 18 carbon atoms; and (C) a silicone.

<2> The hair cosmetic composition according to <1>, wherein R¹ in formula (1) is a linear or branched alkyl group or alkenyl group preferably having 13 to 17 carbon atoms, more preferably having 15 to 17 carbon atoms.

<3> The hair cosmetic composition according to <1> or <2>, wherein R² in formula (1) is preferably an ethylene group or a trimethylene group.

<4> The hair cosmetic composition according to any one of <1> to <3>, wherein R¹, R⁴, and R⁵ in formula (1) are independently preferably a methyl group, an ethyl group, a hydroxyethyl group, or a hydroxypropyl group, more preferably a methyl group or an ethyl group, further preferably a methyl group.

<5> The hair cosmetic composition according to any one of <1> to <4>, wherein a content of the ingredient (A) is preferably 0.1 mass % or more, more preferably 1 mass % or more, further preferably 2 mass % or more, and is preferably 10 mass % or less, more preferably 7 mass % or less, further preferably 6 mass % or less, further preferably 5 mass % or less.

<6> The hair cosmetic composition according to any one of <1> to <5>, wherein the ingredient (B) is preferably one or more selected from the group consisting of myristyl alcohol, cetyl alcohol, stearyl alcohol, and oleyl alcohol, more preferably one or two selected from the group consisting of cetyl alcohol and stearyl alcohol.

<7> The hair cosmetic composition according to any one of <1> to <6>, wherein a content of the ingredient (B) is preferably 0.5 mass % or more, more preferably 1 mass % or more, further preferably 3 masse or more, further preferably 4 mass % or more, further preferably 5 mass % or more, and is preferably 15 mass % or less, more preferably 10 mass % or less, further preferably 8 mass % or less.

<8> The hair cosmetic composition according to any one of <1> to <7>, wherein a molar ratio of the ingredient (B) to the ingredient (A), (B)/(A), is preferably 2.9 or less, more preferably 2.8 or less, further preferably 2.7 or less, and is preferably 2 or more, more preferably 2.2 or more, further preferably 2.4 or more.

<9> The hair cosmetic composition according to any one of <1> to <8>, wherein the ingredient (C) is preferably one or more selected from the group consisting of dimethyl polysiloxane, cyclic silicone, amino-modified silicone, dimethiconol, polyether-modified silicone, polyglycidol-modified silicone, methylphenyl polysiloxane, fatty acid-modified silicone, alcohol-modified silicone, alkoxy-modified silicone, epoxy-modified silicone, fluorine-modified silicone, and alkyl-modified silicone, more preferably one or more selected from the group consisting of dimethyl polysiloxane and amino-modified silicone.

<10> The hair cosmetic composition according to any one of <1> to <9>, wherein a weight-average molecular weight of the silicone which serves as the ingredient (C) is preferably 200,000 or less, more preferably 180,000 or less, further preferably 106,000 or less, further preferably 70,000 or less, and a molecular weight of the silicone which serves as the ingredient (C) is preferably 236 or more, more preferably 450 or more.

<11> The hair cosmetic composition according to any one of <1> to <10>, wherein a content of the ingredient (C) is preferably 0.1 mass % or more, more preferably 0.3 mass % or more, further preferably 0.5 mass % or more, and is preferably 10 mass % or less, more preferably 5 mass % or less, further preferably 3 mass % or less, further preferably 2 mass % or less.

<12> The hair cosmetic composition according to any one of <1> to <11>, wherein a mass ratio of the ingredient (C) to the ingredient (A), (C)/(A), is preferably 0.8 or less, more preferably 0.5 or less, and is preferably 0.01 or more, more preferably 0.1 or more, further preferably 0.2 or more.

<13> The hair cosmetic composition according to any one of <1> to <12>, preferably further comprising the ingredient (D) below:

(D) a monovalent to trivalent fatty alcohol having 1 to 6 carbon atoms or aromatic alcohol having 7 to 10 carbon atoms which is liquid at room temperature.

<14> The hair cosmetic composition according to <13>, wherein the ingredient (D) is preferably one or more selected from the group consisting of isopropyl alcohol, butanediol, propylene glycol, dipropylene glycol, benzyl alcohol, benzyloxyethanol, and phenoxyethanol.

<15> The hair cosmetic composition according to <13> or <14>, wherein a content of the ingredient (D) is preferably 0.01 mass % or more, more preferably 0.05 mass % or more, further preferably 0.1 mass % or more, further preferably 0.5 mass % or more, and is preferably 10 mass % or less, more preferably 5 masse or less, further preferably 3 mass % or less.

<16> The hair cosmetic composition according to any one of <1> to <15>, preferably further comprising the ingredient (E):

(E) an organic acid having 8 or less carbon atoms.

<17> The hair cosmetic composition according to <16>, wherein the ingredient (E) is preferably one or more selected from the group consisting of lactic acid, citric acid, malic acid, and glycolic acid.

<18> The hair cosmetic composition according to <16> or <17>, wherein a content of the ingredient (E) is preferably 0.01 mass % or more, more preferably 0.05 mass % or more, further preferably 0.1 mass % or more, and is preferably 5 mass % or less, more preferably 3 mass % or less, further preferably 1 mass % or less.

<19> The hair cosmetic composition according to any one of <1> to <18>, preferably further comprising the ingredient (F) below:

(F) a liquid oil agent.

<20> The hair cosmetic composition according to <19>, wherein the ingredient (F) is one or more selected from the group consisting of hydrocarbons, ester oils, and vegetable oils.

<21> The hair cosmetic composition according to <19> or <20>, wherein a viscosity (25° C.) of the ingredient (F) is preferably 100 mPa·s or less.

<22> The hair cosmetic composition according to any one of <19> to <21>, wherein a viscosity (25° C.) of the ingredient (F) is preferably 1 mPa·s or more.

<23> The hair cosmetic composition according to any one of <19> to <22>, wherein a content of the ingredient (F) is preferably 0.01 mass % or more, more preferably 0.05 mass % or more, further preferably 0.1 mass % or more, and is preferably 10 mass % or less, more preferably 5 mass % or less, further preferably 4 mass % or less, further preferably 3 mass % or less, further preferably 2 mass % or less.

<24> The hair cosmetic composition according to any one of <1> to <23>, wherein a pH at 25° C. when the hair cosmetic composition is diluted with water to 20 fold by mass is preferably 2.5 or more, more preferably 3.0 or more, and is preferably 6.0 or less, more preferably 5.5 or less, further preferably 5.0 or less.

<25> A method for using a rinse-off-type hair cosmetic composition, the method comprising applying the hair cosmetic composition according to any one of <1> to <24> to hair, and washing away the hair cosmetic composition with water.

EXAMPLES

Examples 1 to 18 and Comparative Examples 1 to 5

Hair conditioners shown in Tables 1 and 2 were prepared and were evaluated according to the following methods and criteria.

(Ease of Separating Hair)

A tress (the entire width: 8 mm) was formed by making two Japanese untreated hair with a length of 7 cm into one set and aligning 5 sets at intervals of about 2 mm. This tress was bleached using hair bleaching agents ("GOLDWELL BLEACH" and "TOPCHIC LOTION 6%" manufactured by GOLDWELL). The hair bleaching was performed by applying the hair bleaching agents in an amount (mass) equal to the hair and rinsing them after hair bleaching at room temperature for 20 minutes. The tress washed using a plain shampoo shown below and rinsed twice, followed by drying, was used as an evaluation tress. The thus dried evaluation tress was immersed in 50 mL of tap water for 30 seconds and thereafter was immersed in 50 mL of a solution of each of the hair conditioners shown in Tables 1 and 2, which was diluted to 10 fold by mass, for 15 seconds, followed by immersion in 200 mL of tap water for 1 minute again and rinsing.

The evaluation was performed using the apparatus shown in FIG. 1. EH5406, manufactured by Panasonic Corporation was used as the dryer, and the settings were Hot (hot air) and set (weak wind). As shown in FIG. 1, the tress after the aforementioned process was set at a distance of 7 cm from the wall and 16 cm from the floor to the tress root, and the heat and airflow which hit the tress were adjusted by directing the hot air of the dryer to the x mark located directly below the tress so as not to directly hit the tress and blowing the air at a distance of 34 cm from the x mark at an angle of 45° with respect to the vertical direction.

By the aforementioned procedure, the time from the start of blowing the air to the time when the tress with two hair adhering into one was separated one by one was measured.

| Formulation of plain shampoo (pH 7.0) | (mass %) |
|---|---|
| 25% polyoxyethylene (2.5) lauryl ether sulfate sodium salt | 62.0 |
| Lauric acid diethanolamide | 2.3 |
| Edetate disodium | 0.15 |
| Sodium benzoate | 0.5 |
| Sodium chloride | 0.8 |
| 75% phosphoric acid | q.s. |
| Perfume and methylparaben | Trace amount |
| Purified water | Balance |
| Total | 100.0 |

(Rapid Drying Properties)

A tress formed by transplanting 30-cm healthy straight blonde Caucasian hair at a graft angle of 60° with a density of 200 strands/cm$^2$ in a 6 cm×6 cm square area and three roots per hole was used for evaluating the rapid drying properties.

The mass of the tress in a dry state was preliminary measured. This tress was washed using the aforementioned plain shampoo and rinsed twice, and 2 g of each hair conditioner shown in Tables 1 and 2 was applied thereto, followed by rinsing with tap water. After the rinsing, the tress was adjusted so as to have a moisture content of 6 g and was placed on a paper towel (BLLEAIR PROWIPE, manufactured by DAIO PAPER CORPORATION), and further, the same paper towel, an acrylic plate, and a weight (where the total weight of the acrylic plate and the weight was 1.4 kg) were sequentially put further thereon, which were allowed to stand for 20 seconds to remove excess moisture.

A shaker (SHK-COCK2, manufactured by Scinics Corporation) was fixed with its dial side (switch) facing downward, and the tress was set therein with the hair tips facing downward and was shaken for 30 seconds (where the shaking speed was set to 170 head swings/minute, and the oscillation width was 3 cm).

Thereafter, hot air was blown toward the center of the tress by the dryer at a distance of 110 cm from the test tress. EH5406, manufactured by Panasonic Electric Works Co., Ltd., was used as the dryer, and the settings were Hot (hot air) and set (weak wind). After blowing air, the mass of the tress was measured every minute, and the measurement was ended at the time when the measured value returns to about the mass of the dry tress (within +0.05 g).

(Sensory Evaluation)

The "smoothness in application" and "smoothness of hair after drying" in practical use were evaluated by three expert panelists into 5 grades (5: very good, 4: good, 3: neither good nor bad, 2: not very good, 1: not good), and averages are shown.

TABLE 1

| | | Examples | | | | | | | | |
|---|---|---|---|---|---|---|---|---|---|---|
| | (mass %) | 1 | 2 | 3 | 4 | 5 | 6 | 7 | 8 | 9 |
| (A) | Palmitamidopropyltrimonium chloride (*1) | 4.20 | 4.20 | 4.20 | 4.20 | 4.20 | 4.20 | 4.20 | 4.20 | 4.20 |
| (A') | Steartrimonium chloride (*2) | — | — | — | — | — | — | — | — | — |
| (B) | Cetyl alcohol (*3) | 6.74 | 7.42 | 6.74 | 6.74 | — | 6.74 | 6.74 | 6.74 | 6.74 |
| | Cetearyl alcohol (*4) | — | — | — | — | 7.07 | — | — | — | — |
| (B') | Behenyl alcohol (*5) | — | — | — | — | — | — | — | — | — |
| (C) | Dimethicone mixture (*6) | 1.00 | 1.00 | — | — | 1.00 | 100 | 1.00 | 1.00 | 1.00 |
| | Dimethicone (*7) | — | — | 1.00 | — | — | — | — | — | — |
| | Bis-cetearyl amodimethicone (*8) | — | — | — | 1.00 | — | — | — | — | — |
| (D) | Dipropylene glycol | 4.00 | 4.00 | 4.00 | 4.00 | 4.00 | — | — | 4.00 | 4.00 |
| | Butanediol | — | — | — | — | — | 1.00 | — | — | — |
| | Benzyl alcohol | — | — | — | — | — | — | 1.00 | — | — |

TABLE 1-continued

|   |   | | | | | | | | | |
|---|---|---|---|---|---|---|---|---|---|---|
| (E) | Lactic acid (90 mass %) | 0.30 | 0.30 | 0.30 | 0.30 | 0.30 | 0.30 | 0.30 | 0.30 | 0.30 |
| (F) | Isoparaffin | — | — | — | — | — | — | — | 1.00 | — |
|  | Isopropyl palmitate | — | — | — | — | — | — | — | — | 5.00 |
|  | Jojoba oil | — | — | — | — | — | — | — | — | — |
|  | Perfume | 0.30 | 0.30 | 0.30 | 0.30 | 0.30 | 0.30 | 0.30 | 0.30 | 0.30 |
|  | Purified water | Balance | Balance | Balance | Balance | Balance | Balance | Balance | Balance | Balance |
|  | (B)/(A) (Molar ratio) | 2.6 | 2.85 | 2.6 | 2.6 | 2.6 | 2.6 | 2.6 | 2.6 | 2.6 |
|  | (C)/(A) (Mass ratio) | 0.24 | 0.24 | 0.24 | 0.24 | 0.24 | 0.24 | 0.24 | 0.24 | 0.24 |
|  | Ease of separating hair (sec.) | 75 | 69 | 63 | 95 | 98 | 95 | 94 | 64 | 76 |
|  | Rapid drying properties (min.) | 6 | 6 | 6 | 6 | 5 | 6 | 4 | 6 | 5 |
| Sensory | Smoothness in application | 4.3 | 5 | 4.7 | 4.7 | 5 | 4.3 | 4 | 5 | 4.7 |
| evaluation | Smoothness of hair after drying | 4.3 | 4.7 | 4.3 | 5 | 4.3 | 4.3 | 4.3 | 4.7 | 5 |

|   |   | Examples | | | | | | | | |
|---|---|---|---|---|---|---|---|---|---|---|
|   | (mass %) | 10 | 11 | 12 | 13 | 14 | 15 | 16 | 17 | 18 |
| (A) | Palmitamidopropyltrmonium chloride (*1) | 4.20 | 4.20 | 4.20 | 4.20 | 5.50 | 3.70 | 3.00 | 6.00 | 4.20 |
| (A') | Steartrimonium chloride (*2) | — | — | — | — | — | — | — | — | — |
| (B) | Cetyl alcohol (*3) | 6.74 | 6.74 | 6.74 | 6.74 | 6.74 | 6.74 | — | — | 6.74 |
|  | Cetearyl alcohol (*4) | — | — | — | — | — | — | 5.00 | 10.00 | — |
| (B') | Behenyl alcohol (*5) | — | — | — | — | — | — | — | — | — |
| (C) | Dimethicone mixture (*6) | 1.00 | 1.00 | 1.00 | 1.00 | 1.00 | 1.00 | 1.00 | 1.00 | — |
|  | Dimethicone (*7) | — | — | — | — | — | — | — | — | 3.00 |
|  | Bis-cetearyl amodimethicone (*8) | — | — | — | — | — | — | — | — | — |
| (D) | Dipropylene glycol | 4.00 | — | 4.00 | — | 4.00 | 4.00 | 4.00 | 4.00 | 4.00 |
|  | Butanediol | — | — | — | — | — | — | — | — | — |
|  | Benzyl alcohol | — | — | — | — | — | — | — | — | — |
| (E) | Lactic acid (90 mass %) | 0.30 | 0.30 | — | — | 0.30 | 0.30 | 0.30 | 0.30 | 0.30 |
| (F) | Isoparaffin | — | — | — | — | — | — | — | — | — |
|  | Isopropyl palmitate | — | — | — | — | 1.00 | — | 1.00 | — | — |
|  | Jojoba oil | 3.00 | — | — | — | — | — | — | — | — |
|  | Perfume | 0.30 | 0.30 | 0.30 | 0.30 | 0.30 | 0.30 | 0.30 | 0.30 | 0.30 |
|  | Purified water | Balance | Balance | Balance | Balance | Balance | Balance | Balance | Balance | Balance |
|  | (B)/(A) (Molar ratio) | 2.6 | 2.6 | 2.6 | 2.6 | 2.6 | 2.9 | 2.6 | 2.6 | 2.6 |
|  | (C)/(A) (Mass ratio) | 0.24 | 0.24 | 0.24 | 0.24 | 0.18 | 0.27 | 0.33 | 0.17 | 0.71 |
|  | Ease of separating hair (sec.) | 107 | 70 | 95 | 84 | 78 | 99 | 82 | 97 | 89 |
|  | Rapid drying properties (min.) | 6 | 6 | 6 | 6 | 5 | 6 | 5 | 6 | 6 |
| Sensory | Smoothness in application | 4.7 | 2 | 2.3 | 1.7 | 3 | 4.3 | 3.3 | 4 | 4.3 |
| evaluation | Smoothness of hair after drying | 5 | 3 | 4 | 3 | 4.3 | 4.7 | 4.7 | 4.3 | 4 |

TABLE 2

|   |   | Comparative Examples | | | | |
|---|---|---|---|---|---|---|
|   | (mass %) | 1 | 2 | 3 | 4 | 5 |
| (A) | Palmitamidopropyltrimonium chloride (*1) | — | 4.20 | 4.20 | 4.20 | 4.20 |
| (A') | Steartrimonium chloride (*2) | 4.20 | — | — | — | — |
| (B) | Cetyl alcohol (*3) | 7.60 | 8.00 | 6.74 | 6.83 | — |
|  | Cetearyl alcohol (*4) | — | — | — | — | — |
| (B') | Behenyl alcohol (*5) | — | — | — | — | 9.20 |
| (C) | Dimethicone mixture (*6) | 1.00 | 1.00 | — | 5.00 | 1.00 |
|  | Dimethicone (5 mm²/s; 25° C.) (*7) | — | — | — | — | — |
|  | Bis-cetearyl amodimethicone (*8) | — | — | — | — | — |
| (D) | Dipropylene glycol | 4.00 | 4.00 | 4.00 | 4.00 | 4.00 |
|  | Butanediol | — | — | — | — | — |
|  | Benzyl alcohol | — | — | — | — | — |
| (E) | Lactic acid (90 mass %) | 0.30 | 0.30 | 0.30 | 0.30 | 0.30 |
| (F) | Isoparaffin | — | — | — | — | — |
|  | Isopropyl palmitate | — | — | — | — | — |
|  | Jojoba oil | — | — | — | — | — |
|  | Perfume | 0.30 | 0.30 | 0.30 | 0.30 | 0.30 |
|  | Purified water | Balance | Balance | Balance | Balance | Balance |
|  | [(B) or (B')]/[(A) or (A')] (Molar ratio) | 2.6 | 3.1 | 2.6 | 2.6 | 2.6 |
|  | (C)/[(A) or (A')] (Mass ratio) | 0.24 | 0.24 | 0 | 1.2 | 0.24 |
|  | Ease of separating hair (sec.) | 300 | 225 | 122 | 239 | 300 |
|  | Rapid drying properties (min.) | 10 | 10 | 9 | 10 | 10 |

TABLE 2-continued

|  | (mass %) | Comparative Examples | | | | |
| --- | --- | --- | --- | --- | --- | --- |
|  |  | 1 | 2 | 3 | 4 | 5 |
| Sensory evaluation | Smoothness in application | 5 | 4.7 | 4.7 | 3.7 | 3.3 |
|  | Smoothness of hair after drying | 4.7 | 4.7 | 3 | 3.3 | 4 |

(*1): VARISOFT PATC, manufactured by Evonik Japan Co., Ltd. (60 mass %; the values in the tables are active amounts)
(*2): QUARTAMIN 86W, manufactured by Kao Corporation (28 mass %; the values in the tables are active amounts)
(*3): KALCOL 6098, manufactured by Kao Corporation
(*4): KALCOL 6870, manufactured by Kao Corporation
(*5): KALCOL 220-80, manufactured by Kao Corporation
(*6): Weight-average molecular weight 180,000:Molecular weight 680 = 33:67 (W/W)
(*7): SH200 C Fluid 5cs, manufactured by Dow Corning Toray Co., Ltd. (molecular weight 680)
(*8): XF42-C4570, manufactured by Momentive Performance Materials Japan

The invention claimed is:

1. A hair cosmetic composition comprising:
(A) from 0.1 to 10% of palmitamidopropyl trimonium chloride;
(B) from 0.5 to 15% of a fatty alcohol selected from the group consisting of myristyl alcohol, cetyl alcohol, stearyl alcohol and oleyl alcohol;
(C) from 0.1 to 10% of dimethicone, and
water,
wherein
a molar ratio of (B)/(A) is from 2.0 to 2.9, and
a mass ratio of (C)/(A) is from 0.1 to 0.71.

2. The hair cosmetic composition according to claim 1, wherein a content of the ingredient (A) is from 1 mass % to 10 mass %.

3. The hair cosmetic composition according to claim 1, wherein a content of the ingredient (B) is from 1 mass % to 15 mass %.

4. The hair cosmetic composition according to claim 1, wherein a content of the ingredient (C) is from 0.3 mass % to 10 mass %.

5. The hair cosmetic composition according to claim 1, further comprising an ingredient (D) selected from the group consisting of isopropyl alcohol, butanediol, propylene glycol, dipropylene glycol, benzyl alcohol, benzyloxyethanol, and phenoxyethanol.

6. The hair cosmetic composition according to claim 5, wherein a content of the ingredient (D) is from 0.01 mass % to 10 mass %.

7. The hair cosmetic composition according to claim 1, further comprising an ingredient (E):
(E) an organic acid having 8 or fewer carbon atoms.

8. The hair cosmetic composition according to claim 7, wherein a content of the ingredient (E) is an 0.01 mass % to 5 mass %.

9. The hair cosmetic composition according to claim 1, further comprising as an ingredient (F) a liquid oil agent.

10. The hair cosmetic composition according to claim 9, wherein the ingredient (F) is at least one selected from the group consisting of a hydrocarbon oil, an ester oil, and a vegetable oil.

11. The hair cosmetic composition according to claim 9, wherein a content of the ingredient (F) is from 0.01 mass % to 10 mass %.

12. A method of applying rinse-off hair cosmetic composition comprising applying a hair cosmetic composition according to claim 1 to the hair and washing away the hair cosmetic composition with water.

13. The hair cosmetic composition according to claim 9, wherein the ingredient (F) is at least one selected from the group consisting of liquid paraffin, isoparaffin, polybutene, isopropyl palmitate, jojoba oil and olive oil.

14. The hair cosmetic composition according to claim 9, wherein a viscosity (25° C.) of the ingredient (F) is 100 mPas or less.

15. The hair cosmetic composition according to claim 1, wherein the molar ratio of the ingredient (B) to the ingredient (A), (B)/(A), is from 2 to 2.8.

16. The hair cosmetic composition according to claim 1, wherein the molar ratio of the ingredient (B) to the ingredient (A), (B)/(A), is from 2 to 2.7.

17. The hair cosmetic composition according to claim 1, wherein the molar ratio of the ingredient (B) to the ingredient (A), (B)/(A), is from 2.2 to 2.8.

18. The hair cosmetic composition according to claim 1, wherein the molar ratio of the ingredient (B) to the ingredient (A), (B)/(A), is from 2.4 to 2.7.

19. The hair cosmetic composition according to claim 1, wherein the molar ratio of the ingredient (B) to the ingredient (A), (B)/(A), is from 2.2 to 2.9.

20. The hair cosmetic composition according to claim 1, wherein the molar ratio of the ingredient (C) to the ingredient (A), (C)/(A), is from 0.2 to 0.71.

21. The hair cosmetic composition according to claim 1, wherein the molar ratio of the ingredient (C) to the ingredient (A), (C)/(A), is from 0.5 to 0.71.

* * * * *